(12) United States Patent
Schneider et al.

(10) Patent No.: US 9,489,731 B2
(45) Date of Patent: Nov. 8, 2016

(54) DIRECTIONAL DIFFUSION FIBER TRACKING

(75) Inventors: Walter Schneider, Pittsburgh, PA (US); Sudhir Pathak, Pittsburgh, PA (US)

(73) Assignee: Universith of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 519 days.

(21) Appl. No.: 14/002,545

(22) PCT Filed: Mar. 15, 2012

(86) PCT No.: PCT/US2012/029229
§ 371 (c)(1),
(2), (4) Date: Dec. 9, 2013

(87) PCT Pub. No.: WO2012/125829
PCT Pub. Date: Sep. 20, 2012

(65) Prior Publication Data
US 2014/0294270 A1    Oct. 2, 2014

Related U.S. Application Data

(60) Provisional application No. 61/452,939, filed on Mar. 15, 2011, provisional application No. 61/467,327, filed on Mar. 24, 2011.

(51) Int. Cl.
*G06T 7/00* (2006.01)
*A61B 5/055* (2006.01)
*A61B 5/107* (2006.01)

(52) U.S. Cl.
CPC .............. *G06T 7/0012* (2013.01); *A61B 5/055* (2013.01); *A61B 5/1075* (2013.01); *G06T 2207/10092* (2013.01); *G06T 2207/30016* (2013.01)

(58) Field of Classification Search
None
See application file for complete search history.

(56) References Cited

U.S. PATENT DOCUMENTS 6,526,305 B1    2/2003  Mori
6,642,716 B1 *  11/2003 Hoogenraad .... G01R 33/56341
                                        324/309

(Continued)

OTHER PUBLICATIONS

IEEE Trans Med Imaging. Sep. 2010;29(9):1626-35. doi: 10.1109/TMI.2010.2045126. Epub Mar. 18, 2010. Generalized q-sampling imaging. Yeh FC, Wedeen VJ, Tseng WY.

*Primary Examiner* — Vu Le
*Assistant Examiner* — Alexander J Lesnick
(74) *Attorney, Agent, or Firm* — Eckert Seamans Cherin & Mellott, LLC

(57) ABSTRACT

Systems and methods facilitating high definition fiber tracking are disclosed. These systems and methods can utilize a directional Axonal Volume (dAV) value that can quantify the direction and volume of anisotropic water diffusion in axons to assess brain connection integrity. dAV provides a robust and anatomically interpretable measurement of connectivity strength of axon tracts. One method include receiving diffusion magnetic resonance imaging (dMRI) data, quantifying a vector axonal directional diffusion axon volume while removing extracellular isotropic water, segmenting fiber tracks from the data, voxelizing the fiber tracks into voxels, determining voxel dAV values for each voxel and directions, and determining fiber dAV values for each fiber track based on voxel dAV values. This non-invasive method can measure strength and integrity of brain tracts. Such measurements aid in detection of connection disorders like traumatic brain injury and mapping the location of brain tracts and their projection fields to improve neurosurgical outcomes.

20 Claims, 13 Drawing Sheets

(56) References Cited

U.S. PATENT DOCUMENTS

| | | |
|---|---|---|
| 2003/0214289 A1 | 11/2003 | van Muiswinkel et al. |
| 2008/0205733 A1* | 8/2008 | Laidlaw .................. A61B 5/055 382/131 |
| 2009/0010517 A1 | 1/2009 | Basser et al. |
| 2010/0004527 A1* | 1/2010 | Dale ................. G01R 33/56341 600/410 |
| 2010/0079140 A1* | 4/2010 | Holthuizen ......... G01R 33/5608 324/307 |
| 2012/0002851 A1* | 1/2012 | Jensen ............. G01R 33/56341 382/128 |

* cited by examiner

DIRECTIONAL DIFFUSION FIBER TRACKING

CROSS-REFERENCE TO RELATED APPLICATIONS

This application claims the benefit of U.S. Provisional Patent application Ser. No. 61/452,939 entitled 'DIRECTIONAL DIFFUSION FIBER TRACKING' and filed Mar. 15, 2011 and claims the benefit of U.S. Provisional Patent application Ser. No. 61/467,327 entitled 'DIRECTIONAL DIFFUSION FIBER TRACKING' and filed Mar. 24, 2011. The entireties of the above-noted applications are incorporated by reference herein.

NOTICE ON GOVERNMENT FUNDING

This innovation was made with government support under NBCHC070104 awarded by Defense Award Research Projects Agency (DARPA). The government has certain rights in the innovation.

TECHNICAL FIELD

The innovation is directed to a novel Magnetic Resonance Imaging (MRI) system and method of directional diffusion fiber tracking. More particularly, the metrics can be directly related to axon tracts which provide a method that can successfully follow brain tracts through fiber crossings.

BACKGROUND

Diffusion Magnetic Resonance Imaging (Diffusion MRI or dMRI) is a form of MRI that allows measurements of the diffusion of water (or other molecules) in biological tissue and has multiple applications. Diffusion weighted Magnetic Resonance Imaging (DWI) can provide a unique ability to quantify the diffusion characteristics of biological tissue. Diffusion processes can be influenced by the geometrical structure of the local environment, which can be used to probe the microstructure of biological tissue non-invasively via diffusion imaging techniques. One application of Diffusion MRI measurement is to quantify diffusion anisotropy of white matter tissue, such as for tracking neural fibers. The goal of fiber tracking is to accurately follow and quantify fibers through their entire length without interference from other fibers or other tissue and correctly getting from source to termination. Anisotropy in biological tissue can be measured by a Fractional Anisotropy (FA) map based on Diffusion Tensor Imaging and is the basis of most tractography methods. Anisotropic measurement based on FA has limitations due to its directional insensitivity and instability to the effects of crossing fibers. Other methods include variations on FA, such as Generalized Fractional Anisotropy (gFA), which can be used for advanced reconstruction methods like QBALL Imaging and Diffusion Spectrum Imaging. Some metrics like the Westin metric can classify voxels as isotropic, single fiber or crossing fiber structure. Some of these metrics are robust for describing the isotropic and anisotropic measure of a single fiber, but unreliable for a crossing fiber.

Conventional metrics such as FA have multiple drawbacks when used for fiber tracking. FA is a scalar metric which is proportional to the standard deviation of values of diffusion anisotropy in all direction at a given location. FA has two fundamental limitations. First, because it is a measure based on standard deviation, it works well for isotropic and single fiber cases, but fails in fiber crossing situations, because it combines anisotropic information from all directions. Second, FA does not provide a connectivity metric between functional regions of the human brain. It is difficult to predict axon connectivity based on the FA metric. FA is dependent on interstitial water, compression/spreading of the fiber tract, tract crossing, and local curvature. These tendencies make FA a badly confounded measure of brain connectivity.

The mismatch of a standard deviation measure such as FA and a mean measure can be seen via an analogy to measuring the strength of I-beams in a building. Engineers use finite element models that verify that each I-beam has the strength (e.g., can support a mean weight 50 tons) to support the load at that point. Using a standard deviation measure (e.g., the standard deviation of each I-Beam is 1 ton) would be a poor measure of the key variable—the load that link could support. Having beams with a 1 ton standard deviation rather than a 5 ton standard deviation does not tell you if beam will support a 50 ton weight, because standard deviation is a poor measure of the strength of a building link.

A core goal for fiber tracking is to quantify the volume of axons oriented in a specific direction within a voxel. However, FA quantifies the variance of the three principal directions, removing information regarding either the direction or count of axons in a voxel. FA is both directionless and dimensionless. While these qualities may be appealing to mathematicians, they make FA less useful for applications measurement of connective strength.

Anisotropy or connectivity is directionally dependent by nature, which scalar field quantities like FA are unable to describe. Conventional metrics are not direction sensitive, because all conventional metrics since the introduction of FA in 1990 by Moseley et al. have been scalar metrics. Another characteristics of connectivity not represented by conventional metrics such as FA that are based on the standard deviation or related quantities is the strength or magnitude of diffusion in a given voxel. Because of this, conventional metrics lack the needed reliability in fiber crossing area and strength to provide a real anatomical quantification.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The subject innovation, in various aspects, comprises systems and methods that facilitate high definition fiber tracking (HDFT). These systems and methods can be based on a directional Axonal Volume (dAV) vector value that can quantify the direction and volume of anisotropic water diffusion in axons for the purposes of assessing the integrity brain connections. dAV provides a robust and anatomically interpretable measurement of connectivity strength of brain axon tracts. Such a method can include the acts of receiving a diffusion magnetic resonance imaging (dMRI) dataset, quantifying a vector quantity of axonal directional diffusion while removing the extracellular isotropic water, segmenting one or more diffusion directions from the dMRI dataset, voxelizing each of the one or more fiber tracks into a plurality of voxels, determining a voxel dAV value for each of the plurality of voxels and directions, and determining a fiber dAV value for each of the one or more fiber tracks based at least in part on the voxel dAV values. This provides a non-invasive method to measure the strength and integrity of brain tracts. Such measurement can add in the detection of brain connection disorders such as traumatic brain injury as well as mapping the location of brain tracts and their projection fields to improve neurosurgical outcomes.

In one aspect, the subject innovation can comprise a system that facilitates high definition fiber tracking (HDFT). Such a system can comprise a data acquisition component that can obtain a diffusion magnetic resonance imaging (MRI) dataset and a segmentation component that can facilitate segmentation of one or more fiber tracks from the dataset. In addition, the system can include a voxelization component that can voxelize each of the one or more fiber tracks into a plurality of voxels and an anisotropy component that can determine a voxel directional Axonal Volume (dAV) value for each of the plurality of voxels.

In other aspects, the subject innovation can comprise a method that facilitates HDFT. Such a method can include the acts of receiving a diffusion magnetic resonance imaging (MRI) dataset and segmenting one or more fiber tracks from the diffusion MRI dataset. Additionally, the method can include the steps of voxelizing each of the one or more fiber tracks into a plurality of voxels associated with the fiber track, determining a voxel directional Axonal Volume (dAV) value for each of the plurality of voxels, and determining a fiber dAV value for each of the one or more fiber tracks. The fiber dAV value for each of the one or more fiber tracks can be based at least in part on the voxel dAV value for each of the plurality of voxels associated with the fiber track.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
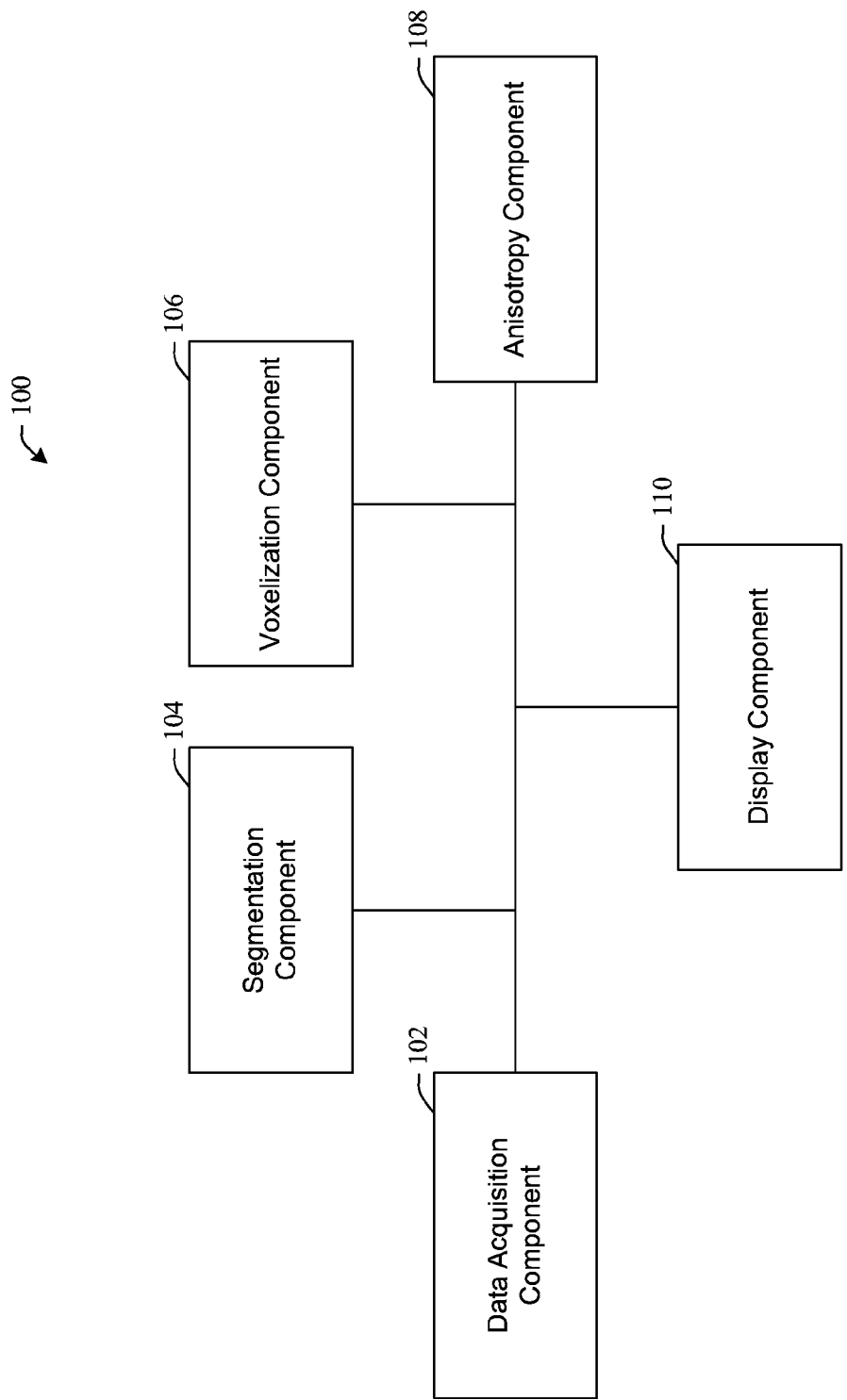
FIG. 1 illustrates a system capable of facilitating high definition fiber tracking (HDFT) in accordance with aspects of the subject innovation.

The innovation is now described with references to the drawings, wherein reference numerals are used to refer to corresponding drawings throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

In various aspects, the subject innovation relates to a novel diffusion MRI (dMRI)-based map referred to herein as directional Axonal Volume (dAV), which can quantify an amount of anisotropic water in one or more given directions and can also estimate isotropic water content. As described further herein, the subject innovation can employ the directional sensitivity of dAV to map its value along a fiber track. In various embodiments, systems and methods of the subject innovation can provide a connectivity measure between corresponding functional regions, which, in contrast to prior art techniques, is unconfounded by other crossing fibers.

Systems and methods of the subject innovation can be employed to quantify or describe connectivity between function region of human brain. dAV provides an accurate metric capable of describing the strength of connections, in contrast to conventional metrics. The most widely used conventional metric, Fractional anisotropy (FA), basically describes how much water is hindered at a given location in brain. This metric is derived from the Diffusion Tensor via Diffusion Tensor Imaging (DTI) and, for that reason, has widely acknowledged limitations. Related conventional measures derived from DTI like Mean Diffusivity (MD), Westin measure (cl, cp, cs), etc., are all limited due to the inherent limitations of DTI-based reconstruction methods. Other conventional methods such as advanced diffusion methods like QBALL, Constrained spherical deconvolution, PAS MRI, etc., have some success at resolving fiber crossings, but are ineffective at measuring connectivity and fail to provide anatomically meaningful units for measuring connectivity.

In prior work discussing generalized q-sampling imaging (GQI), Yeh et al. discussed methods related to using q-space diffusion MRI data to describe an Orientation Distribution Function (ODF). In various aspects, this subject innovation can apply ODF in novel ways and utilize ODF measurements and quantities derived therefrom to calculate an amount of water inside an axonal bundle. This subject innovation can also utilize these ODF measurements and derive quantities for describing how much water is present in the extra-cellular matrix. This subject innovation employs a novel way to calculate these anatomically related measurements called dAV (directional Axonal Volume) for a fiber bundle in a human brain.

dAV can be used by this subject innovation as a biomarker for anisotropic water content in biological tissue. In a manner analogous to X-rays for bones, systems and methods employing dAV can allow visualization and quantification of the integrity of brain tracts. This subject innovation can allow clinicians to visualize and quantify the integrity of 40+ tracts in the brain. These tracts, much like bones, are the support structures for a normal brain. In the past, damage to these support structures could rarely be detected. However, this subject innovation, with dAV and HDFT methods, can facilitate visualization and quantification of brain connectivity disorders such as the breaks in traumatic brain injury, developmentally altered wiring in autism, and neurodegeneration in Huntington's and Alzheimer's diseases.

In addition to the scalar nature of conventional anisotropic measurements, they are all also based on voxels. Although measurements in accordance with the subject innovation can be done voxel-wise, dAV can use fiber tracking and ODF (model free) information to describe amounts of water inside fiber bundles. Conventional ODF provides information about diffusion in a voxel. However, it fails to provide information as a whole about a fiber bundle. The subject innovation can also employ dAV as a connectivity measure between two functional regions which are unable to be described by a voxel based measurement.

This subject innovation has a wide range of potential applications, both in research and clinically. For example, it can be utilized in statistical experiments in group studies or with brain pathology. Systems and methods employing dAV can also provide a robust determination of the Grey-White Matter boundary. Accordingly, the subject innovation can be used to create a well-defined White Matter surface and can also be used in fiber tractography as a stopping criterion. The fiber stopping capability of this subject innovation can provide a fiber end point projection on Cortical and/or sub-cortical regions.

As explained in greater detail below, dAV can provide a robust and anatomically related anisotropic measurement to describe connectivity strength between two functional regions with substantially better accuracy than FA based methods. dAV is a vector quantity, which makes it directionally sensitive and therefore can be robust in fiber crossing regions, in contract to FA or gFA, which provide scalar quantity for crossing regions. dAV can provide multiple advantages not available in conventional techniques. These include, first, a direct measure of connective strength in anatomically meaningful units (mL of water in axons), unconfounded by interstitial fluid, crossing fibers (e.g., at angles more than the resolution of the ODF separation), and changes in fiber tract packing that confound FA and gFA based methods. Second, dAV can provide a more effective stopping rule and well defined cortical surface without the need for T1 segmentation and realignment. Third, dAV can facilitate more accurate following of tracts to the cortical surface. Fourth, dAV calculation of connective strength is robust with respect to the choice of the number of streamlines. Fifth, dAV can provide identification of location with single, double and triple crossing. These features make dAV based anisotropic measurement a realistic, anatomically quantitative, and directionally sensitive anisotropic diffusion measurement that can be used to describe water content along fiber tracks.

Some techniques can improve the accuracy of dAV in certain situations, such as when two parallel fiber pass through the same location. dAV at that location as described herein can be the sum of the dAV of those fiber tracks. These situations are common near cortex where U-fiber (or short range fibers) run parallel to long range fiber tracks. The dAV value can be corrected by subtracting dAV values from other location within the same fiber bundles.

Additionally, calibration techniques can be used to find actual concentration of water associated with dAV measurements. For example, using a phantom filled with mixture of different concentration of deuterium dioxide and water, dAV measurements can be taken to obtain values that can be used to normalize dAV values to the actual quantity of water in the phantom.

The subject innovation can provide numerous advantages over conventional systems and methods. By using techniques described herein, quantities of isotropic and anisotropic water can be distinguished and quantified, thus allowing the subject innovation to remain unconfounded by interstitial water such as from edema. In contrast, conventional techniques of imaging fiber track are ambiguous during brain swelling over the acute phase of diseases and disorders, when accurate diagnosis and treatment is most important. Systems and methods of the subject innovation can obtain results despite the edema, etc., providing useful data months before existing methods.

In other aspects, the subject innovation can be employed to identify and image neural tracts. As will be understood, this innovation can have applicability to a range of clinical disorders and research applications.

The subject innovation can be used to locate and quantitatively describe each of the major fiber tracts in a subject's brain. It can quantify the quality of the fiber tract measurement and quantify its volume, connectivity, and integrity. This information can be used in a variety of research and clinical settings. These applications can include Traumatic Brain Injury (TBI), presurgical planning, post-surgical assessment, and genetic brain disorders such as autism, etc. Genetic brain disorders can be diagnosed, for example, by using techniques of the subject innovation by comparing one or more regions of a subject brain to normal and disordered examples of the same region.

In aspects, information obtained by techniques of the subject information (e.g., tract locations, etc.) can be provided before, after, or during a surgical procedure to assist with determining the potential or actual impact of the procedure on neural fibers. By monitoring the locations of tools used during a procedure and providing fiber tract information obtained from the subject innovation in connection with those locations to represent the proximity of the instruments to one or more fiber tracts during the procedure. This information can also be used for presurgical planning to choose a route, port location, etc. so as to minimize fiber damage.

Traumatic brain injuries, strokes, and other conditions can be assessed using information from the subject innovation to determine which tracts are affected and to what extent. This information can be used in treatment to determine, for example, to what extent a user can recover with physical therapy, or which capabilities will likely be lost as a result of the condition.

Referring initially to the drawings, FIG. 1 illustrates a system 100 capable of facilitating high definition fiber tracking (HDFT) in accordance with aspects of the subject innovation. System 100 can comprise a data acquisition component 102 that can obtain or receive diffusion data (e.g., a diffusion magnetic resonance dataset, etc.). This information can be obtained locally (e.g., from diffusion magnetic resonance imaging (diffusion MRI) data obtained by an MRI scanner collocated with system 100) in some embodiments, or can be obtained remotely in other embodiments. System 100 can also include a segmentation component 104 that can segment or facilitate segmentation of fiber tracts. In various embodiments, segmentation can be performed manually or in a partly or wholly automatic manner, such as via segmentation component 104. Voxelization component 106 can voxelize each of the fibers segmented by segmentation component 104 into a plurality of voxels.

For each of the plurality of voxels associated with each fiber, anisotropy component 108 can determine the directional Axonal Volume (dAV) for each voxel of the plurality of voxels. Additionally, anisotropy component 108 can determine a dAV of each of the fibers based at least in part on the dAV determined for the voxels associated with the fiber. In further aspects, anisotropy component 108 can determine a measure of isotropic water content associated with the voxels and/or fibers.

System 100 can also include a display component 110 that can provide results obtained by system 100 to a user or other entity. These results can be presented in a variety of formats, such as 3-dimensional data, which can include dAV for some or all of the voxels, such as dAV information graphically displayed along fibers, etc. In other aspects, a white matter and grey matter boundary can be modeled, e.g., by using the dAV value as a stopping criterion to distinguish between white matter and gray matter. Additionally, display component 110 can provide further information, such as a fiber map of all or a portion of a subject's brain, comparisons with earlier images of the same subject's brain (e.g., to monitor development, changes such as post-surgical, etc.), or comparison with one or more of normal brains or brains with one or more disorders (e.g., to assist diagnosis, determination of impacted regions and/or functions, etc.).

The following is an overview of some of the theory underpinning concepts and techniques used in connection with systems and methods of the subject innovation. Diffusion MRI can measure a probability distribution of the displacement of water molecules in a given voxel. The relationship between diffusion MR Signals $S(k,q)$, spin density $\rho(r)$, and the average propagator $p_A(r,R)$, which describes the probability distribution of the displacement of water molecules in the diffusion time $\Delta$ can be written as shown in equation (1):

$$S(k,q) = \int \rho(r) e^{-2\pi i k \cdot r} \int p_\Delta(r,R) e^{2\pi i q \cdot R} dR dr \qquad (1)$$

where r is the voxel coordinate and R is the diffusion displacement within voxel. After integrating with respect to k (also referred to as k-space reconstruction), diffusion weighted image data $W(r,q)$ can be obtained, which is related to the underlying diffusion propagator $p_\Delta(r,R)$ as shown in equation (2):

$$W(r,q) = \int \rho(r) p_\Delta(r,R) e^{2\pi i q \cdot R} dR \qquad (2)$$

Applying an inverse Fourier transform gives equation (3):

$$P_\Delta(r,R) = \int W(r,q) e^{-2\pi i q \cdot R} dq \qquad (3)$$

where $P_\Delta(r,R) = \rho(r) p_\Delta(r,R)$.

In many diffusion reconstruction methods, the probability distribution function (PDF) from equation (3) is projected onto a unit sphere in the diffusion displacement space to calculate peaks of diffusion on the sphere; the projected probability distribution function is called the Orientation Distribution Function (ODF). Mathematically, the orientation distribution function $\psi_Q(r, \hat{u})$ can be calculated by integrating probability distribution function radially, as shown in equation (4):

$$\psi_Q(r,\hat{u}) = \int_0^{L_\Delta} P_\Delta(r, L\hat{u}) dL \qquad (4)$$

Where $L_\Delta$ is the mean diffusion displacement in the diffusion time $\Delta$. ODF is a function of $\hat{u}$, which are unit vectors on the sphere representing anisotropy in corresponding direction. By substituting equation (3) into (4) and simplifying, a relationship between diffusion signals, q-vectors and the unit vectors on the sphere can be derived, as seen in equation (5):

$$\psi_Q(r,\hat{u}) = L_\Delta \int W(r,q) \mathrm{sinc}(2\pi L_\Delta q \cdot \hat{u}) dR \qquad (5)$$

The q-vectors and $\hat{u}$ can discretize and can be written in Matrix form as shown in equation (6):

$$\psi_Q(r, \hat{u}) = L_\Delta \sum_q W(r, q) \mathrm{sinc}(2\pi L_\Delta q \cdot \hat{u}) \qquad (6)$$

Equation (5) provides two major information quantities within a voxel: the direction(s) of diffusion and the extent of diffusion in the corresponding direction(s). Systems and methods of the subject innovation can construct a diffusion map based at least in part on the ODF described in equation (5), which can provide an amount of anisotropic water content (e.g., an amount of water diffusing anisotropically) in a voxel. In aspects, this information can be correlated with a fraction of fibers running in a corresponding direction. These features constitute a novel connectivity metric called directional-Axonal Volume (dAV), used in various aspects of the subject innovation. dAV is a vector valued function defined on a unit sphere. ODF, defined in equation (4) above, constitutes two part: isotropic water content (e.g., an amount of water diffusing isotropically), equal to $\min(\psi_Q)$, and Anisotropic water content (e.g., an amount of water diffusing anisotropically). Mathematically, anisotropic water content or directional Axonal Volume (dAV) can be written as in equation (7):

$$\mathrm{dAV}(\vec{r},\hat{u}) = Z_0(\psi_Q(\hat{u}) - \min(\psi_Q)) \qquad (7)$$

Where, $\hat{u}$ is the direction in which dAV is being determined in a voxel (it is to be understood that it can be determined for multiple directions, in that dAV is a vector quantity, and can be projected in any of a plurality of directions to obtain a scalar associated with that direction), $\min(\psi_Q)$ is the isotropic part and $Z_0$ is scaling constant. In aspects, $Z_0$ can be a normalization constant determined across a whole brain, for example, to relate measurements determined as described herein to an actual amount of water content in the brain or in a given voxel. Normalization can be based on measurements of a phantom (e.g., of deuterium dioxide and water, etc.), as described herein. Equation (7) provides a relative anisotropic measure with respect to a complete isotropic voxel. This scaled version of the dAV metric (an unscaled version can omit $Z_0$) can be used to calculate spin density or estimated water content inside voxel. Mathematically, if $(S_x, S_y, S_z)$ is the size of a voxel in millimeters, then the volume of voxel is given by equation (8):

$$V(\vec{r}) = S_x S_y S_z \text{ mm}^3 = S_x S_y S_z \text{ mL} \tag{8}$$

where $\vec{r}$ is the location of the voxel.

Multiplying the volume of the voxel by dAV can provide an estimated amount of directional water content in a given direction $\hat{u}$, as shown in equation (9):

$$dAV(\vec{r}, \hat{u}) V(\vec{r}) = dAV(\hat{u}) S_x S_y S_z \text{ mL} \tag{9}$$

For the isotropic component, which can be described as a largest sphere encompassed by the ODF, the subject innovation can also determine an isotropic water content in a voxel, as seen in equation (10):

$$Z_0 \min(\psi_Q) V(\vec{r}) = Z_0 \min(\psi_Q) S_x S_y S_z \text{ mL} \tag{10}$$

Notably, the dAV based measure does not calculate the actual molar concentration of water in a voxel. Instead, it can determine an approximate value which describes the relationship between spin densities of axonal water which in turn correlates to water content in axons. Systems and methods of the subject innovation can employ this metric to describe the anatomical connectivity measure between functional areas of the brain. The subject innovation can employ this metric to find an axonal volume estimate at each point in fiber tracts.

Figure 2:
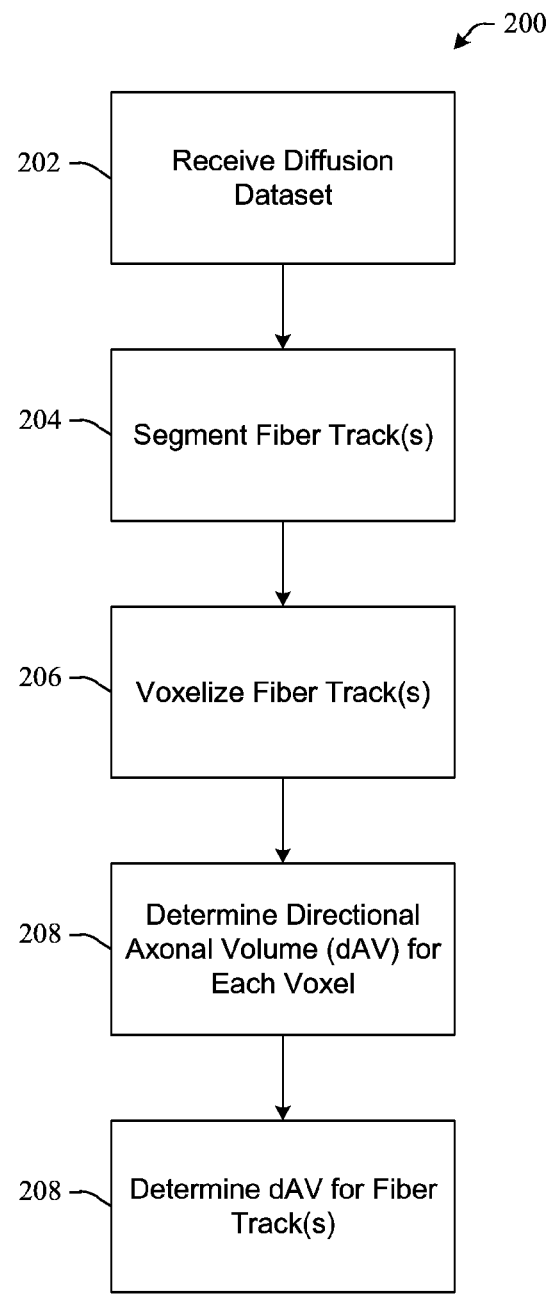
FIG. 2 illustrates a methodology of neural fiber tracking in accordance with an aspect of the innovation.

FIG. 2 illustrates a methodology 200 of neural fiber tracking in accordance with an aspect of the innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Method 200 can facilitate High-Definition Fiber Tracking (HDFT) Fiber Tractography on a brain or portion thereof, which can be based on directional Axonal Volume (dAV) and peaks of an orientation distribution function (ODF) for each voxel in a whole brain (or portion thereof, etc.). A large number of streamlines (fibers) can be calculated according to method 200 to represent the brain or portion thereof (for a whole brain, in various embodiments, the number of streamlines can be greater than or equal to 250,000, although more or less can be used in various embodiments). The method can begin at step 202 wherein image data can be received (e.g., a diffusion dataset). At step 204, one or more fiber tracks (e.g., tracks of interest, such as associated with a particular research, clinical, or other application, etc.) can be segmented (e.g., manually, automatically, etc.). At step 206, the segmented fiber tracks can be voxelized. Fiber tracks are sets of 3D points in the mm coordinate system, and each of these 3D points corresponds to a voxel in 3D diffusion volume. Converting 3D points in mm of a fiber track into a set of voxels is called "voxelization" of a fiber tracks.

Next, at step 208, the dAV can be determined for each voxel in the voxelized fibers, such as described in greater detail elsewhere herein (e.g., as in connection with FIG. 3 below). Next, at step 210, the dAV can be determined for the segmented fiber tracks. The determination of dAV for a set of points p, dAV(p), of a fiber track in step 208 can involve multiple steps and can be determined as follows, where t is a tangent and $\{(\Delta p_i)\}$ are the nearby discrete sampling points (e.g., nearby eight points, etc.). Optionally, the fiber orientations with a quality assurance (QA) measure less than a predetermined QA threshold can be removed from $\{(\Delta p_i)\}$. Also, in some aspects, any fibers that have larger a crossing angle greater than a predetermined crossing angle threshold can also be removed from the $\{(\Delta p_i)\}$. Next, dAV(p) can be defined as an interpolation (e.g., tri-linear, etc.) of dAV at each discrete location $\{(\Delta p_i)\}$. The dAV for each point can then be projected back to the corresponding voxel coordinate, and for each voxel, the mean of projected dAV is calculated. Finally, the dAV of each fiber track can be defined as the sum of all the mean dAV calculated for each projected voxel associated with the fiber track.

dAV can be used in various way to describe voxel based anisotropic diffusion, for example, as a stopping criterion for fiber tractography or to create grey matter and white matter surfaces.

Figure 3:
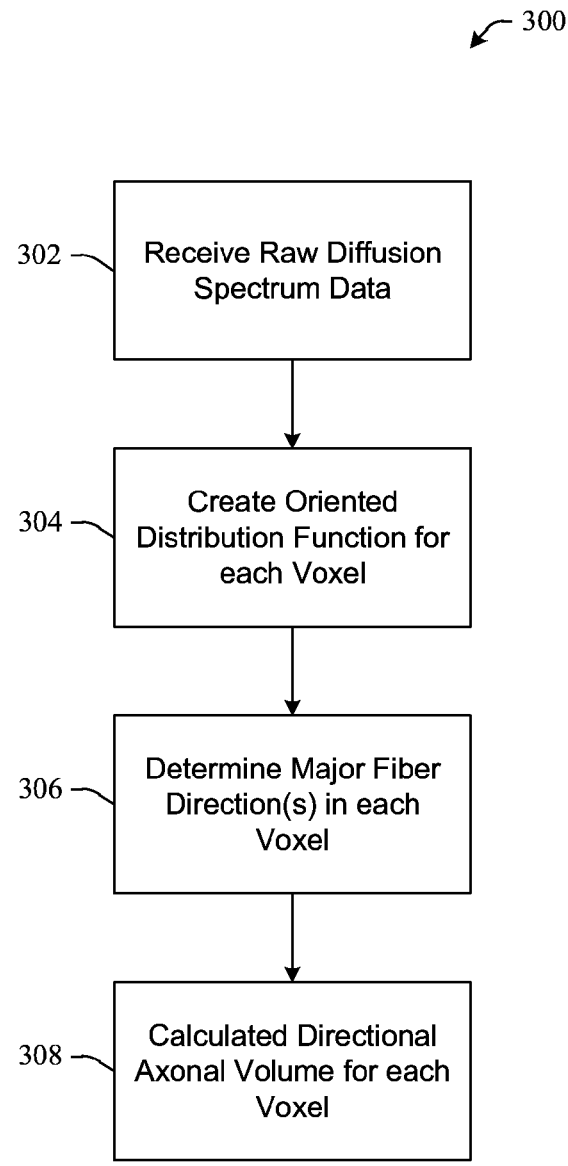
FIG. 3 illustrates a methodology for calculating directional Axonal Volume (dAV) in one or more voxels.

FIG. 3 illustrates a methodology 300 for calculating directional Axonal Volume (dAV) in one or more voxels. The method can begin at 302, where raw diffusion spectrum data can be received. This information can be based on diffusion MRI performed on the region of interest (e.g., brain, portion thereof, etc.) that can be obtained locally or remotely (e.g., in some embodiments, imaging equipment can include the capability to perform techniques described herein; in other embodiments, these techniques can be performed remotely, etc.). At 304, the raw diffusion spectrum data can be used to create an Orientation Distribution Function (ODF) for each voxel of the image dataset as described elsewhere herein. In aspects, the ODF can be created using Generalized q-sampling Imaging (GQI) reconstruction (e.g., using 257 gradient directions for reconstruction, although in various aspects, more or less could be used, etc.), although in various aspects, other reconstruction techniques can be used. GQI is a q-space reconstruction method based on matrix multiplication useable to reconstruct an ODF from any of a variety of sets of diffusion data (e.g., diffusion spectrum imaging (DSI), etc.).

Next, at 306, the major fiber direction(s) can be determined for each voxel based at least in part on the ODF. The peaks of the ODF can be calculated for each voxel, by finding local maxima of the ODF value over a discrete sphere. The directions of these peaks correspond to the major fiber direction(s) in each voxel. Finally, at step 308, the directional Axonal Volume (dAV) can be calculated for each voxel, based at least in part on the determined fiber direction(s) and values of the ODF, as described above.

Figure 4:
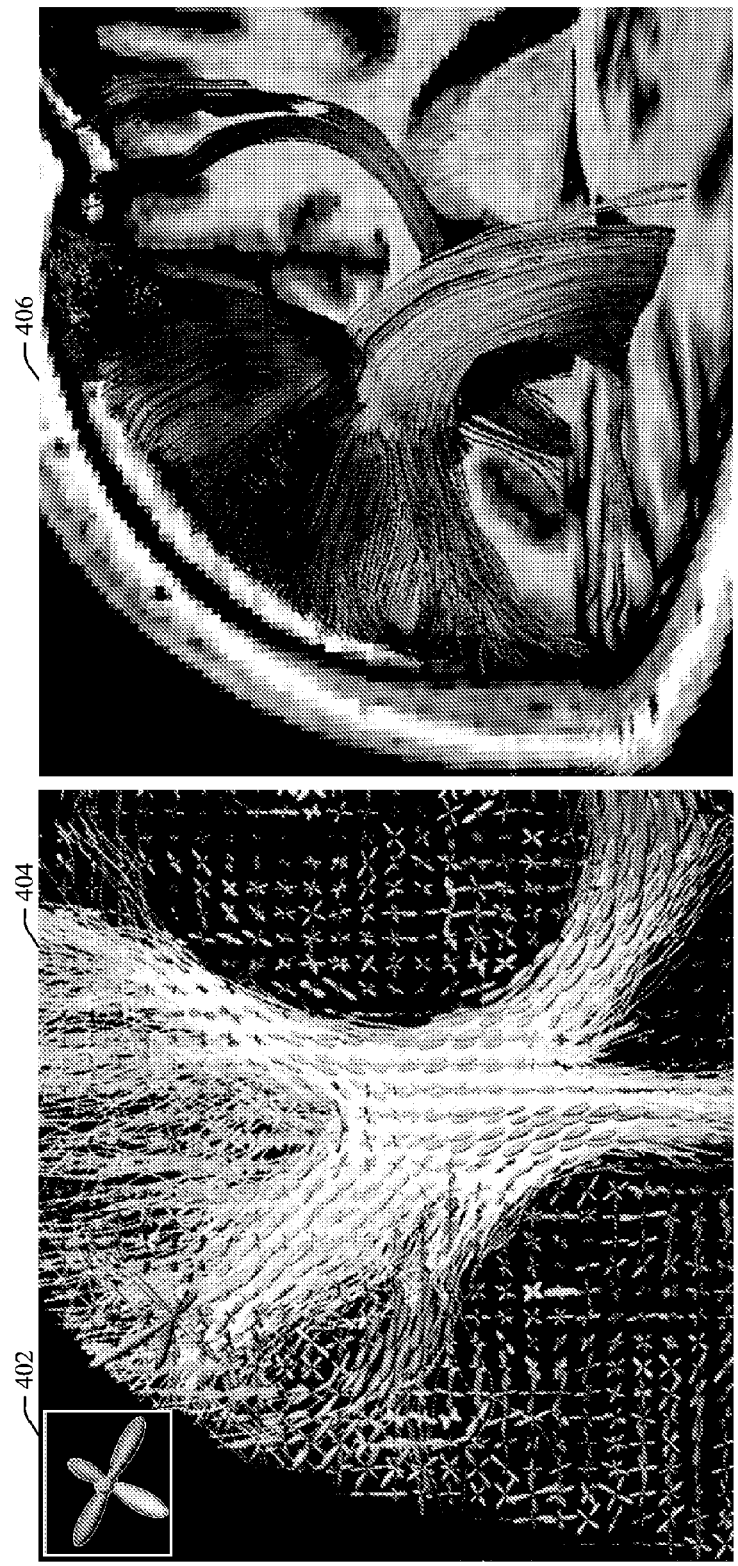
FIG. 4 shows three images relating to example aspects of application of the method illustrated in FIG. 3.
Figure 5:
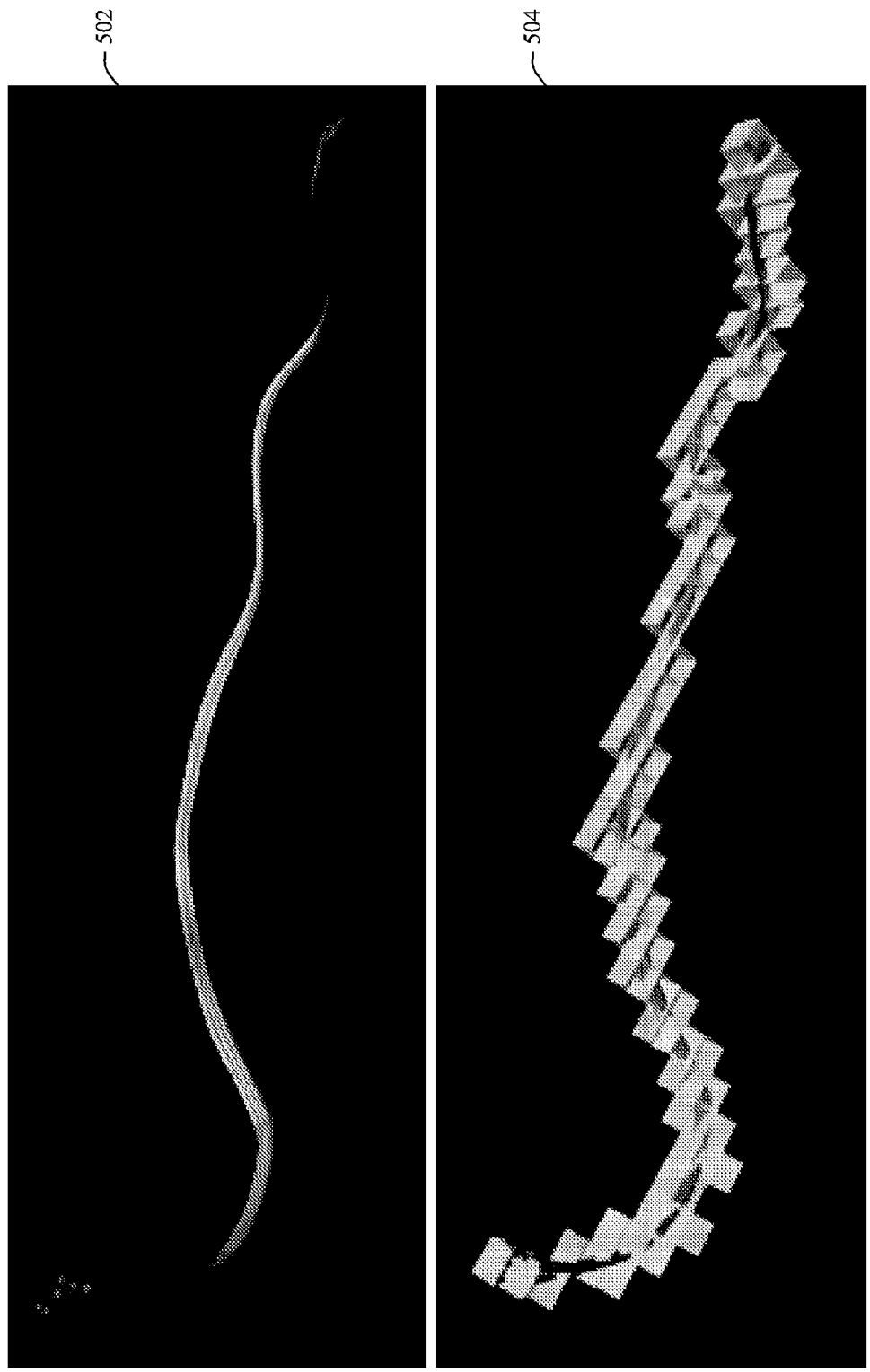
FIG. 5 shows images illustrating calculation of dAV along fiber tracks.
Figure 6:
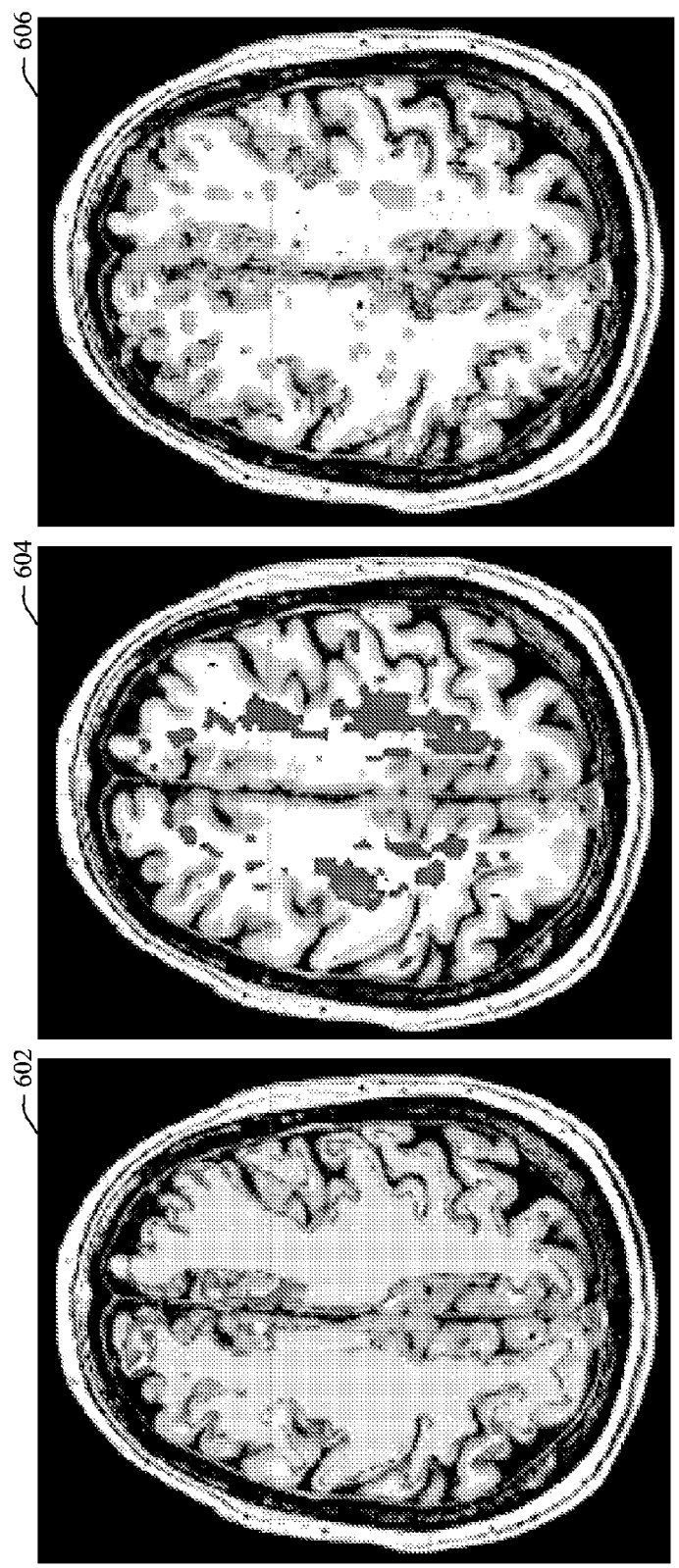
FIG. 6 illustrates the directional nature of dAV, showing three dominant fiber directions.

FIG. 4 shows three images 402-406 illustrating example aspects of application of the subject innovation. The whole brain can be parceled into voxels. Image 402 (the inset) shows the water in a single voxel containing a triple crossing of fibers. The size of the ellipse represents the amount of water in axons oriented in that direction. The principle axis of the ellipse shows the direction of those axons. Image 404 shows a coronal brain slice with the set of voxels overlaid on the structural MRI image with the white showing the core of the white matter tracts. The white shows what a traditional structural MRI image provides, showing there is a tract but not the number, direction or the magnitudes of the crossing tracts. The ellipses show the dAV estimated volumes of each tract. Image 406 shows the HDFT constructed fiber tracts generated from making streamlines of the voxel diffusion data of Image 404. FIG. 5 shows images illustrating calculation of dAV along fiber tracks. Image 502 shows segmented fiber tracks with dAV projection along the track indicating via color, and image 504 illustrates voxelization of the segmented fiber tracks. FIG. 6 illustrates the directional nature of dAV, showing three dominant fiber directions, with a first dominant fiber direction shown in 602, a second dominant fiber direction shown in 604, and a third dominant fiber direction shown in 606.

To aid in the understanding of the aspects of the subject innovation, experimental results associated with specific experiments that were conducted are discussed herein. However, although for the purposes of obtaining the results discussed herein, specific choices were made as to the selection of various aspects of the experiments and associated setups—such as choice of reconstruction algorithms, imaging equipment, values of parameters employed in algorithms, or other aspects—the systems and methods described herein can be employed in other contexts, as well.

In one experiment, a 62-year-old female subject was scanned using a 3T MRI system (TIM Trio, Siemens, Erlangen, Germany). The scan was done on a 32-channel coil, using a single-shot twice-refocused echo planar imaging (EPI) diffusion pulse sequence. On the same subject, single-shell and grid sampling schemes (also known as the high angular resolution diffraction imaging (HARDI) and diffusion spectrum imaging (DSI) sampling schemes, respectively) were acquired by the same spatial parameters: the field of view was 240 mm×240 mm, matrix size 96×96, slice thickness 2.4 mm (with no gap), and the number of the slices was 50 to cover the cerebral cortex, resulting in a voxel size of 2.4 mm×2.4 mm×2.4 mm. For the grid-sampling scheme, the number of gradient directions was 257, with a maximum b-value=7000 sec/mm$^2$, and TR/TE=9916 ms/157 ms, resulting in a scanning time of around 45 minutes. The generalized q-sampling reconstruction was applied to sampling schemes with a diffusion sampling length ratio of 1.25, as recommended in the original GQI study. The ODF dimension of 642 was used, resulting in an ODF angular resolution of 9 degrees. The streamline algorithm and HDFT were conducted using the following parameters: an angular threshold of 60 degrees and a step size=1.25 (half of the spatial resolution). An FA threshold of 0.12 and a dAV threshold of 0.65 were assigned. Magnetization Prepared Rapid Gradient Echo (MPRAGE) was employed with the following parameters: TR=2110 ms, TE=2.63 ms, flip angle=8 degrees, 176 slices, FoV=256× 256 mm$^2$, and voxel size=1.0 mm$^3$. Fiber Tracking was performed using HDFT, with fiber tracks segmented manually. dAV and gFA were calculated for the dataset using equations described above, and dAV for fiber tracks was calculated using algorithms described above.

The fiber tracking showed high accuracy based on the match of established anatomy of specific tracts, including the corona radiata and the arcuate fasciculus. The experiment compared two examples of processing the same data, dAV-based methods in DSI Studio with HDFT routines compared with TrackVis in connection with two tracts with a set of parameter settings representative of parameters commonly used with the programs. The experiment looked at whether the dAV stopping rule would provide a better termination stopping performance, reducing the problems of streamline surfing at the cortex that occurs with FA-based stopping rules. A common practice in programs such as TrackVis is to set a small turn radius (e.g., 20° per millimeter) to suppress the streamline surfing, which produce serious artifacts such as having streamlines make circles in the cortical mantel ending in the wrong hemisphere or skull. However, the negative consequence of a restricted turning angle is that it makes following tracts difficult in the white matter when axons turn at a faster rate. Normal axons can turn sharply (e.g., 90° in a millimeter, etc.). In this case, using the same input DSI data set, the experiment contrasted typical parameter setting for TrackVis FA based fiber tracking with HDFT based fiber tracking with the turning radius parameter for both methods.

dAV quantifies spin density in each direction in a voxel, giving a quantitative measure of anisotropy water content in a given direction. dAV can be used as an anatomically relevant metric to describe connectivity between functional regions. Table 1 describes isotropic and dAV values of three major dominant fiber directions in Grey Matter (GM), White Matter (WM), cerebrospinal fluid (CSF) and Thalamus from the experiment:

TABLE 1

| Tissue | Isotropic Water | First Anisotropic | Second Anisotropic | Third Anisotropic |
| --- | --- | --- | --- | --- |
| GM | 50.8933 mL | 5.8293 mL | 3.3249 mL | 2.1842 mL |
| WM | 59.8209 mL | 17.3698 mL | 4.3200 mL | 1.5428 mL |
| CSF | 3.5323 mL | 0.3787 mL | 0.1716 mL | 0.1393 mL |
| Thalamus | 1.5557 mL | 0.4736 mL | 0.1464 mL | 0.0961 mL |

Table 2 describes mean and standard deviation of dAV values for the different tissue types:

TABLE 2

| Tissue Type | Mean dAV (mL) | Standard Deviation of dAV |
| --- | --- | --- |
| Grey Matter | 0.2074 | 0.0079 |
| White Matter | 0.5460 | 0.0227 |
| CSF | 0.2143 | 0.0128 |
| Thalamus | 0.2723 | 0.0149 |

Figure 7:
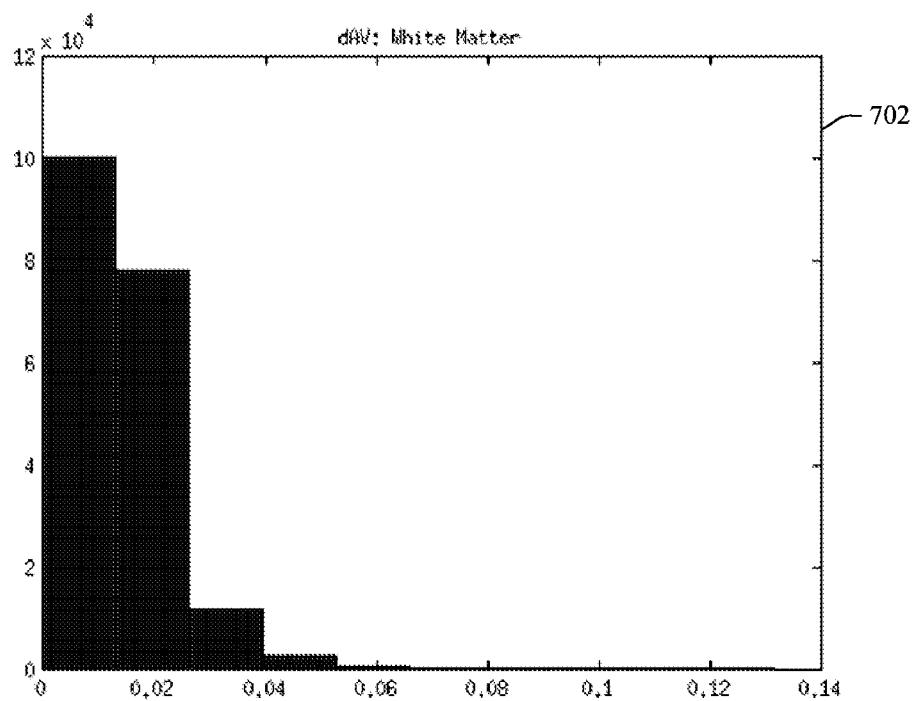
FIG. 7 shows histogram plots indicating dAV magnitude in white matter and grey matter.
Figure 7:
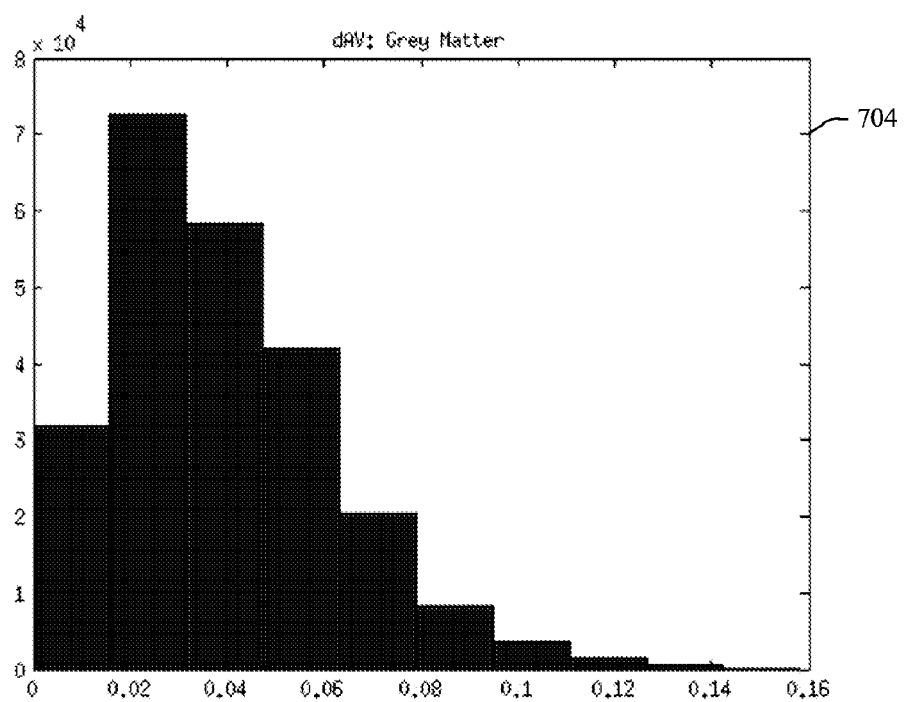
Figure 8:
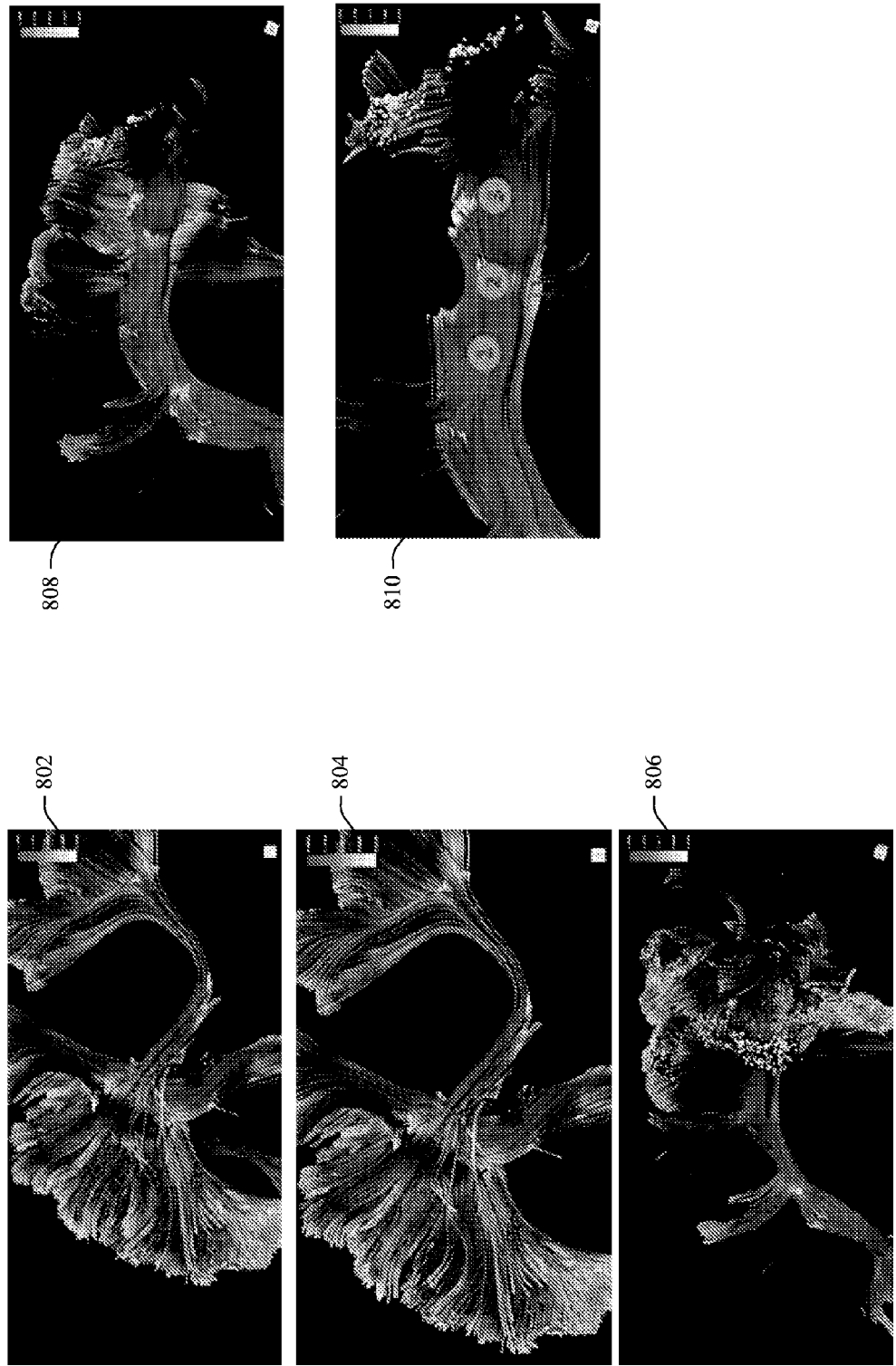
FIG. 8 shows dAV maps of three fiber tracks, the Corticospinal, Corpus Callosum and Superior Longitudinal, in a major triple crossing in the semioval center region of the human brain.

As expected, White matter has more anisotropy than Grey Matter and significantly more dAV. A t-test between GM and WM population showed significant difference between GM and WM voxels with p at or around 0%. FIG. 7 shows histogram plots indicating dAV magnitude in white matter at 702 and grey matter at 704. As seen in FIG. 7, dAV can effectively distinguish between grey and white matter. These quantitative values can be used to estimate an anatomically related anisotropic measure of water content in a given voxel from the dAV.

dAV is directionally sensitive, which enable this metric to provide an insensitive anisotropic measure of water content along fiber tracks in fiber crossing areas in White matter. FIG. 8 shows dAV maps of three fiber tracks, the Corticospinal, Corpus Callosum and Superior Longitudinal, in a major triple crossing in the semioval center region of the human brain, in images 802, 804, 806, 808, and 810. Using techniques discussed herein, the isotropic and anisotropic components of water in each voxel can be separated. In experiments conducted herein, dAV was calculated along fiber tracks, along with the dAV of fiber crossings, and gFA was determined along fiber tracks. Table 3 shows the correlation between dAV of fiber tracks with gFA, dAV of crossing fiber with gFA and dAV of fiber tracks and dAV of crossing fibers:

TABLE 3

| Correlation Coefficient | dAV of Fiber | dAV of Crossing Fiber | g-Fractional Anisotropy |
|---|---|---|---|
| dAV of Fiber | 1.00 | −0.061 | 0.964 |
| dAV of Crossing Fiber | −0.061 | 1.00 | −0.505 |
| g-Fractional Anisotropy | 0.964 | −0.505 | 1.00 |

As seen in Table 3, the dAV of fiber tracks is independent of dAV of crossing fibers (r=−0.061), but gFA demonstrates substantial dependency on the crossing tract (r=−0.505). This shows that gFA combines information of anisotropy in all directions and makes it a confounded measure for connectivity, but that dAV is able to distinguish fiber crossings.

Figure 9:
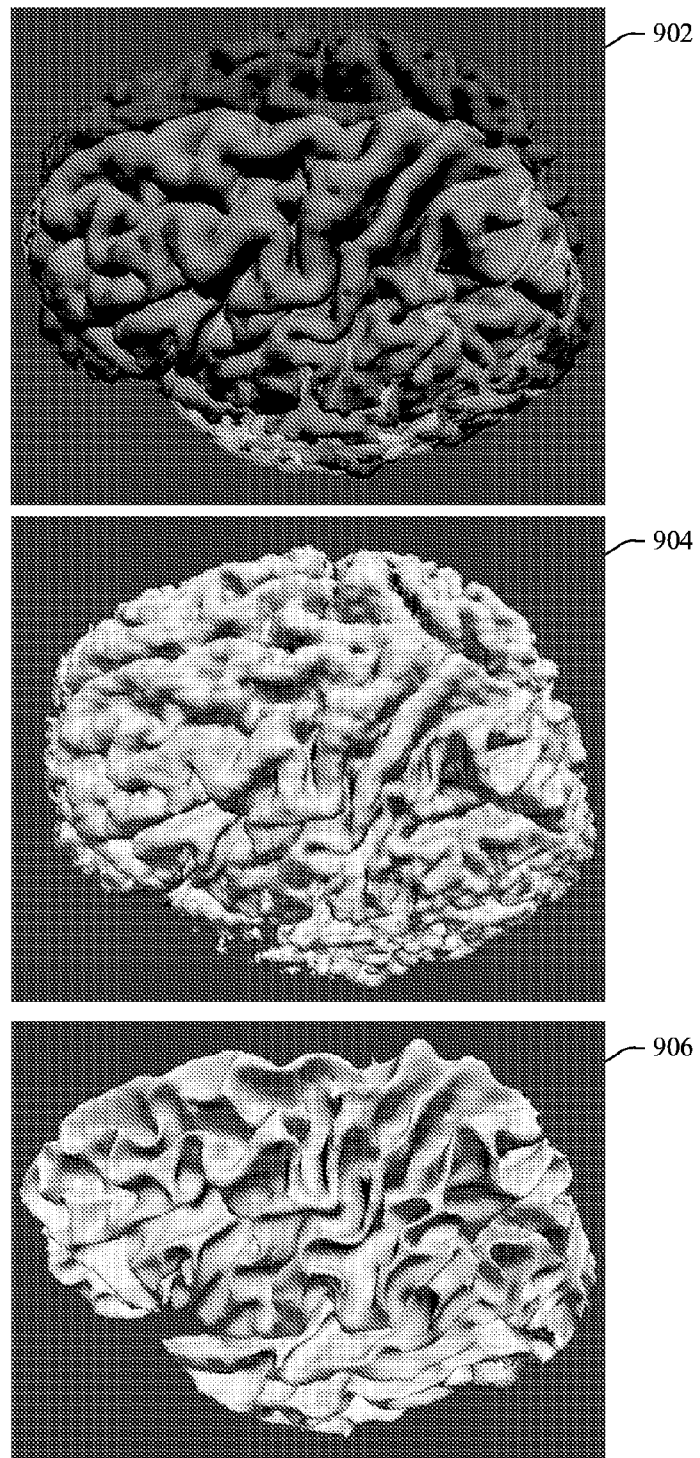
FIG. 9 shows a comparison between surface reconstruction using contours of dAV of major Fiber Tracks vs. a prior technique for surface reconstruction.
Figure 10:
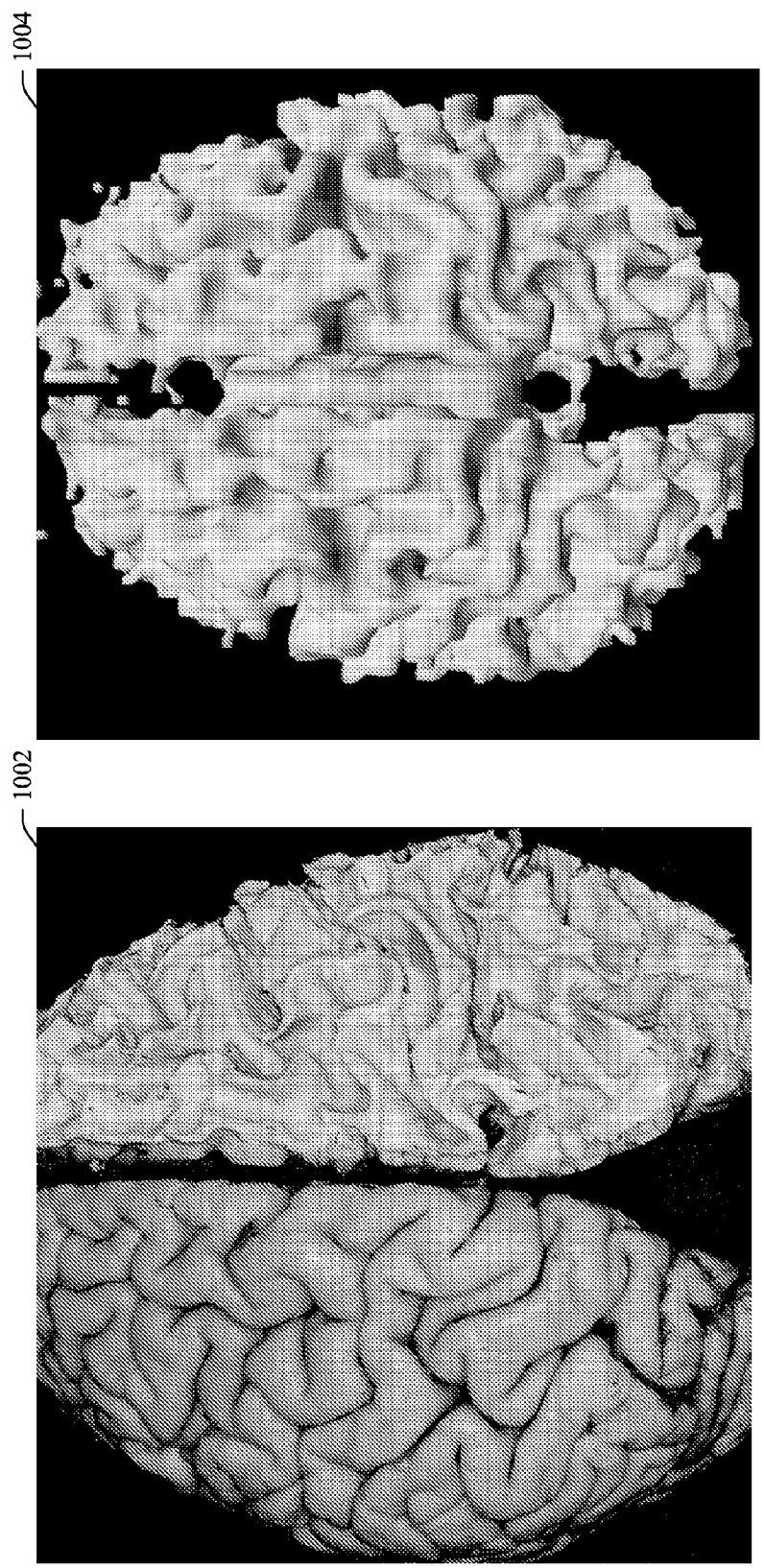
FIG. 10 shows a comparison between Dissected Grey matter and White matter surfaces, and a dAV surface reconstruction.

FIG. 9 shows a comparison between surface reconstruction using contours of dAV of major Fiber Tracks vs. a prior technique (Freesurfer) for surface reconstruction. Image 902 shows a Grey Matter surface reconstruction using Freesurfer (in Blue) and contours of dAV. Image 904 shows surface reconstruction using contours of dAV, and 906 shows surface reconstruction using the Freesurfer technique. White matter surface visualization provides sulci and gryi identification of Cortex in Human brain. Because dAV quantifies Quantitative measure of spin density, it can accurately identify Grey Matter and White Matter boundary. The contours of dAV can be used to create White matter and Grey Matter surface as shown in FIG. 9. Comparison between dAV based Grey/White Matter Surface with the Freesurfer surface shows significant agreement with the surface from dAV, as shown in FIG. 9. FIG. 10 shows a comparison between Dissected Grey matter and White matter surfaces in 1002, and a dAV surface reconstruction, at 1004.

Fiber Tractography can find connectivity between functional regions of human brain. A major assumption in Fiber tractography processing is that the direction tangent to fiber tracts is proportional to the major diffusion direction of the underlying voxel. Major parameters in Fiber Tractography include stopping rules and angular threshold. Stopping rules constrain fiber tracks to enter into Grey Matter. However, conventional methods can't robustly identify the White Matter and Grey Matter boundary. In contrast, dAV can provide a better stopping criterion in Fiber Tractography algorithms, because it is a quantitative measure that clearly shows discontinuity at the grey matter and white matter boundary and hence can be used to identify the boundary. In aspects, a projection map can be created using endpoints of the fiber tracks. These projection fields allow creating a somatotopic map of different cortical and subcortical regions.

Figure 11:
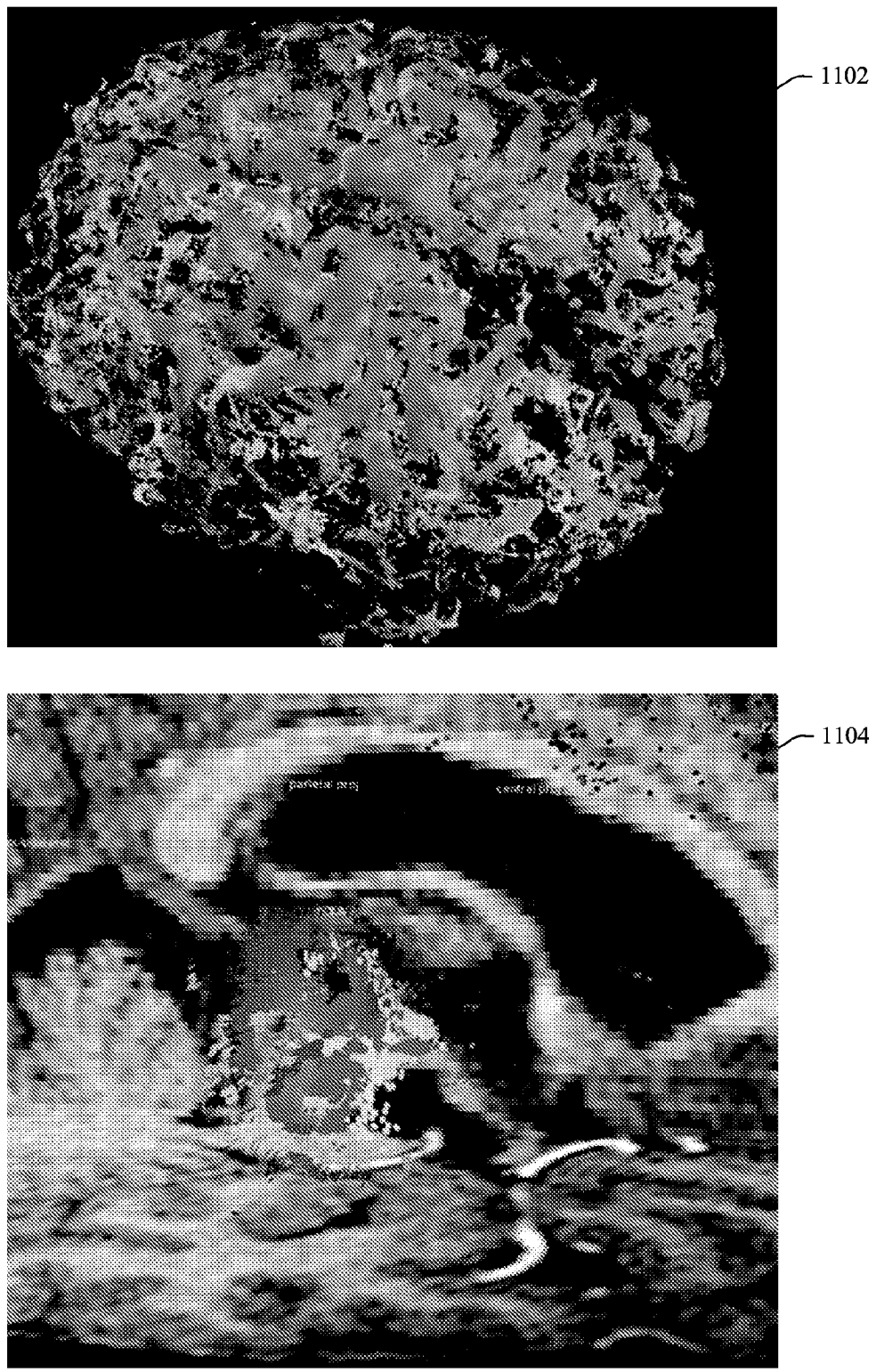
FIG. 11 shows a projection map or field for fiber tracks.

FIG. 11 shows a projection map or field for fiber tracks. At 1102, end point projections of whole brain fiber tracks can be seen, as determined from dAV. Image 1104 shows endpoint projections of Thalamic fiber tracks on the Thalamus surface.

Fiber Tracks in Tractography are basically a simulated path of a bundle of axons. The number of fiber tracks is a parameter that can either be set by a user or can be constant for whole brain tracking. Because the underlying connectivity doesn't depend on how many fiber tracks are selected in Tractography, a robust metric is needed which is independent of the number of fibers. dAV, as described in greater detail elsewhere herein, can satisfy this need. dAV is robust with respect to fiber count.

Figure 12:
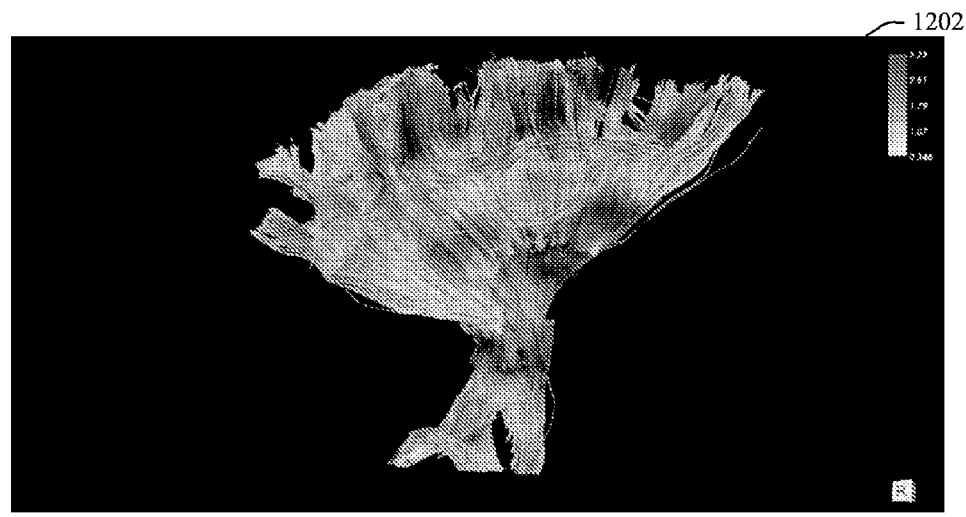
FIG. 12 shows the robustness of dAV in Corticospinal tracks with respect to changes in fiber count.
Figure 12:
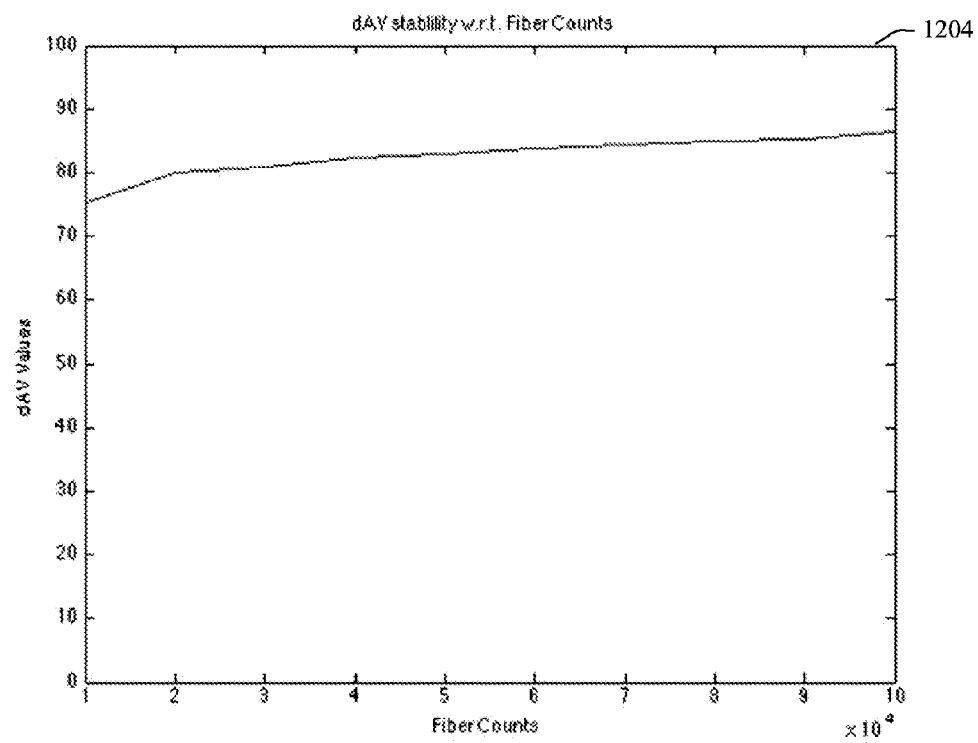

FIG. 12 shows the robustness of dAV in Corticospinal tracks with respect to changes in fiber count. Image 1202 shows the Corticospinal tracks with dAV used as a color code. Graph 1204 shows a plot of dAV values with respect to fiber count. The coefficient of variation of dAV value for the Corticospinal track with respect to the number of fibers was 4.5%. These results show that dAV provides a robust and anatomically relevant metric to describe strength of connectivity between two regions in Human brain.

Experiments applying the subject innovation in connection with other tracts showed other advantages of dAV. For example, the dorsal corona radiata is an unusual tract that makes very slow curves from above the internal capsule. Hence the accuracy in TrackVis is good with the smaller turn angle of 20° and false alarms becoming a serious problem with a turn radius of 40°, producing anatomically wrong projection fields. In contrast, HDFT of the subject innovation showed little variation in accuracy for the corona radiate, which would be expected if the dAV termination stopped the streamline surfing (and hence avoided an increase in error with the wider turn angle). Results showed metrics of the subject innovation are substantially better than the TrackVis accuracy.

However, significant improvements over conventional techniques were seen for the arcuate. The fibers of the arcuate can make sharp turns as they turn from the core tract as they move to their cortical projection site. In both program there is a sharp drop in hits and increase in dropouts for the small turn angle due to producing fiber stubs that stop at the position of the turn without projection to the cortex. Using the larger turn angle produces a clear improvement in the arcuate with no loss for HDFT processing path based on dAV. In contrast, TrackVis with FA-based stopping produces artifacts with a sharp turning rate and hence does very poorly for the arcuate.

Figure 13:
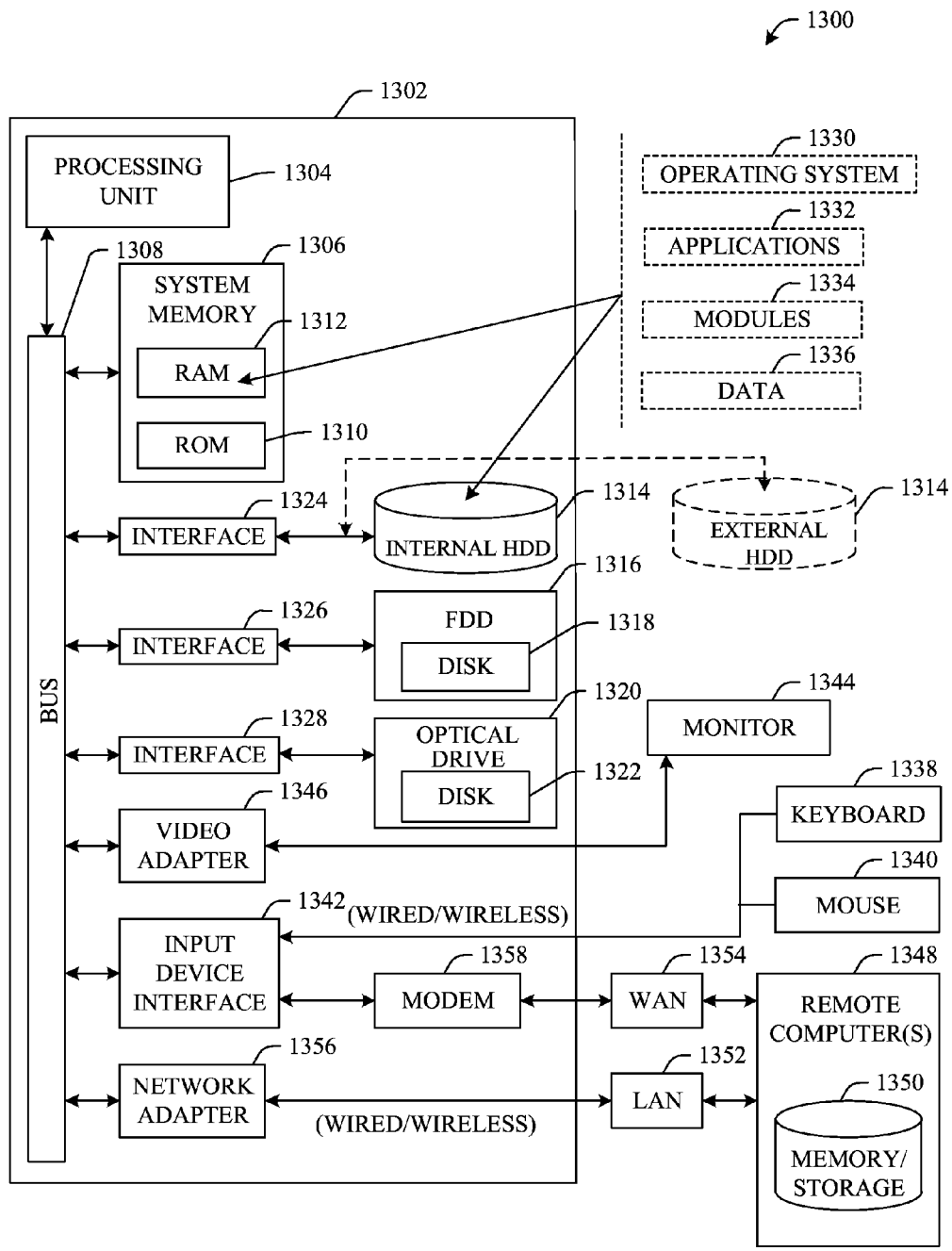
FIG. 13 illustrates a block diagram of a computer operable to execute the disclosed architecture.

Referring now to FIG. 13, there is illustrated a block diagram of a computer operable to execute the disclosed architecture. Various aspects of the subject innovation can be implemented in connection with a computer. In order to provide additional context for these and other aspects of the subject innovation, FIG. 13 and the following discussion are intended to provide a brief, general description of a suitable computing environment 1300 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 13, the exemplary environment 1300 for implementing various aspects of the innovation includes a computer 1302, the computer 1302 including a processing unit 1304, a system memory 1306 and a system bus 1308. The system bus 1308 couples system components including, but not limited to, the system memory 1306 to the processing unit 1304. The processing unit 1304 can be any of various commercially available processors. Dual microprocessors and other multi-processor architectures may also be employed as the processing unit 1304.

The system bus 1308 can be any of several types of bus structure that may further interconnect to a memory bus (with or without a memory controller), a peripheral bus, and a local bus using any of a variety of commercially available bus architectures. The system memory 1306 includes read-only memory (ROM) 1310 and random access memory (RAM) 1312. A basic input/output system (BIOS) is stored in a non-volatile memory 1310 such as ROM, EPROM, EEPROM, which BIOS contains the basic routines that help to transfer information between elements within the computer 1302, such as during start-up. The RAM 1312 can also include a high-speed RAM such as static RAM for caching data.

The computer 1302 further includes an internal hard disk drive (HDD) 1314 (e.g., EIDE, SATA), which internal hard disk drive 1314 may also be configured for external use in a suitable chassis (not shown), a magnetic floppy disk drive (FDD) 1316, (e.g., to read from or write to a removable diskette 1318) and an optical disk drive 1320, (e.g., reading a CD-ROM disk 1322 or, to read from or write to other high capacity optical media such as the DVD). The hard disk drive 1314, magnetic disk drive 1316 and optical disk drive 1320 can be connected to the system bus 1308 by a hard disk drive interface 1324, a magnetic disk drive interface 1326 and an optical drive interface 1328, respectively. The interface 1324 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1302, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1312, including an operating system 1330, one or more application programs 1332, other program modules 1334 and program data 1336. All or portions of the operating system, applications, modules, and/or data can also be cached in the RAM 1312. It is appreciated that the innovation can be implemented with various commercially available operating systems or combinations of operating systems.

A user can enter commands and information into the computer 1302 through one or more wired/wireless input devices, e.g., a keyboard 1338 and a pointing device, such as a mouse 1340. Other input devices (not shown) may include a microphone, an IR remote control, a joystick, a game pad, a stylus pen, touch screen, or the like. These and other input devices are often connected to the processing unit 1304 through an input device interface 1342 that is coupled to the system bus 1308, but can be connected by other interfaces, such as a parallel port, an IEEE 1394 serial port, a game port, a USB port, an IR interface, etc.

A monitor 1344 or other type of display device is also connected to the system bus 1308 via an interface, such as a video adapter 1346. In addition to the monitor 1344, a computer typically includes other peripheral output devices (not shown), such as speakers, printers, etc.

The computer 1302 may operate in a networked environment using logical connections via wired and/or wireless communications to one or more remote computers, such as a remote computer(s) 1348. The remote computer(s) 1348 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1350 is illustrated. The logical connections depicted include wired/ wireless connectivity to a local area network (LAN) 1352 and/or larger networks, e.g., a wide area network (WAN) 1354. Such LAN and WAN networking environments are commonplace in offices and companies, and facilitate enterprise-wide computer networks, such as intranets, all of which may connect to a global communications network, e.g., the Internet.

When used in a LAN networking environment, the computer 1302 is connected to the local network 1352 through a wired and/or wireless communication network interface or adapter 1356. The adapter 1356 may facilitate wired or wireless communication to the LAN 1352, which may also include a wireless access point disposed thereon for communicating with the wireless adapter 1356.

When used in a WAN networking environment, the computer 1302 can include a modem 1358, or is connected to a communications server on the WAN 1354, or has other means for establishing communications over the WAN 1354, such as by way of the Internet. The modem 1358, which can be internal or external and a wired or wireless device, is connected to the system bus 1308 via the serial port interface 1342. In a networked environment, program modules depicted relative to the computer 1302, or portions thereof, can be stored in the remote memory/storage device 1350. It will be appreciated that the network connections shown are exemplary and other means of establishing a communications link between the computers can be used.

The computer 1302 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11(a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
   a memory that stores computer-executable instruction;
   a processor that executes the computer-executable instructions to perform operations, comprising:
   utilizing magnetic resonance imaging (MRI) diffusion data to map axonal tracts and determine a voxel directional Axonal Volume (dAV) value within a voxel, wherein the dAV determines an amount of anisotropic fluid in a given vector which is a directional axonal volume of water content in axons and determines an amount of isotropic interstitial water content.

2. The system of claim 1, wherein the operations further comprise:
   segmenting one or more fiber tracks from the data;
   voxelizing each of the one or more fiber tracks into a plurality of voxels; and
   determining a directional Axonal Volume (dAV) value for each of the plurality of voxels, wherein the dAV measures anisotropic water content for each fiber direction of the plurality of voxels.

3. The system of claim 2, wherein the operations further comprise
   determining a dAV value along a fiber direction for each of the one or more fiber tracts, wherein the dAV value for each of the one or more fiber tracks is based at least in part on one or more of the voxel dAV values for each of the plurality of voxels.

4. The system of claim 3, wherein the MRI diffusion data is associated with a patient with a traumatic brain injury (TBI), and the fiber dAV value is based at least in part on the TBI.

5. The system of claim 3, wherein the MRI diffusion data is associated with a patient with a genetic brain disorder, and the fiber dAV value is based at least in part on the genetic brain disorder.

6. The system of claim 3, wherein the operations further comprise:
   employing the voxel dAV values as a stopping criteria for the one or more fiber tracks.

7. The system of claim 2, wherein the operations further comprise:
   calculating a quantity of isotropic water within a voxel.

8. The system of claim 1, wherein the operations further comprise:
   obtaining the MRI diffusion data.

9. The system of claim 1, wherein the operations further comprise:
   presenting an image based at least in part on the voxel dAV value along a fiber direction.

10. The system of claim 8, wherein the image is a 3-dimensional image representing a plurality of fiber tracks associated with the MRI diffusion data.

11. The system of claim 1, wherein the MRI diffusion data is based on a human brain, and the voxel dAV value is normalized based at least in part on a quantity of water associated with the human brain.

12. A method of facilitating high definition fiber tracking, comprising:
    receiving a diffusion magnetic resonance imaging (MRI) dataset;
    segmenting one or more fiber tracks from the diffusion MRI dataset;

voxelizing each of the one or more fiber tracks into a plurality of voxels associated with the fiber track;

determining a voxel directional Axonal Volume (dAV) value for each of the plurality of voxels, wherein the dAV determines an amount of anisotropic fluid in a given vector which is a directional axonal volume of water content in axons and determines an amount of isotropic interstitial water content; and determining a fiber dAV value for each of the one or more fiber tracks, wherein the fiber dAV value for each of the one or more fiber tracks is based at least in part on the voxel dAV value for each of the plurality of voxels associated with the fiber track.

13. The method of claim 12, wherein determining the voxel dAV value for each of the plurality of voxels comprises:

creating an orientation distribution function (ODF) for each of the plurality of voxels;

determining a major fiber direction for each of the plurality of voxels; and calculating the voxel dAV value for each of the plurality of voxels, wherein calculating the voxel dAV value is based at least in part on the ODF for each of the plurality of voxels.

14. The method of claim 12, wherein determining the voxel dAV value for each of the plurality of voxels further comprising normalizing the voxel dAV value based at least in part on a normalization constant determined for a brain associated with the dataset.

15. The method of claim 12, wherein segmenting the one or more fiber tracks comprises employing at least a subset of the voxel dAV values for each of the plurality of voxels as a stopping criterion.

16. The method of claim 12, further comprising representing the one or more fiber tracks as a 3-dimensional image.

17. The method of claim 12, further comprising:

comparing the one or more fiber dAV values to at least one reference dataset; and diagnosing a genetic brain disorder based at least in part on the comparing.

18. The method of claim 12, further comprising diagnosing a traumatic brain injury based at least in part on the one or more fiber dAV values.

19. The method of claim 12, further comprising determining a quantity of isotropic water based at least in part on a subset of the voxel dAVs for each of the plurality of voxels.

20. A method, comprising:

utilizing MRI diffusion data to map axonal tracts that determines a voxel directional Axonal Volume (dAV) value within a voxel, wherein the dAV determines an amount of anisotropic fluid in a given vector which is a directional axonal volume of water content in axons and determines an amount of isotropic interstitial water content.

* * * * *